Figure 1:
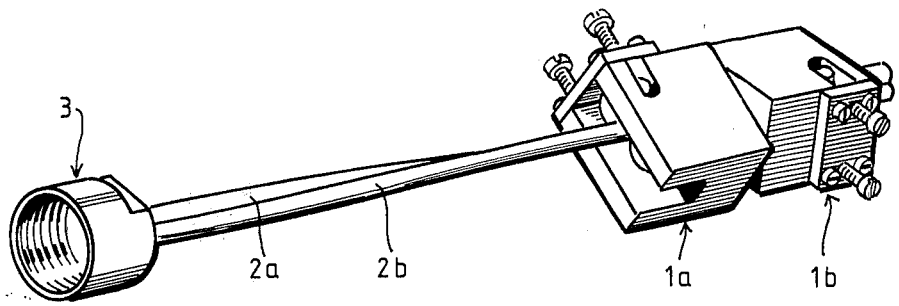

United States Patent [19]

Axelsson

[11] 4,259,949
[45] Apr. 7, 1981

[54] ANTI-FRICTION SCREW AND NUT ASSEMBLY

[75] Inventor: Robert Axelsson, Huskvarna, Sweden

[73] Assignee: Een-Holmgren Ortopediska AB, Sweden

[21] Appl. No.: 9,898

[22] Filed: Feb. 6, 1979

[30] Foreign Application Priority Data

Feb. 8, 1978 [SE] Sweden ............................... 7801490

[51] Int. Cl.³ ............................................... A61F 5/10
[52] U.S. Cl. .................................... 128/77; 128/25 R; 3/1; 74/424.8 R; 74/424.8 NA; 74/89.15; 248/118
[58] Field of Search ..................... 128/77, 80 G, 80 R, 128/83, 94, 165, 82, 87 R, 84, 88, 25 R, 25 B, 26; 272/67, 68; 273/189 R, 189 A; 74/424.8 R, 424.8 NA, 89.15, 84, 426; 248/118; 403/81; 46/68, 85; 3/1

[56] References Cited

U.S. PATENT DOCUMENTS

| 560,281 | 5/1896 | Rauhoff | 74/424.8 R |
|---|---|---|---|
| 1,583,219 | 5/1926 | Anderson, Jr. et al. | 74/424.8 R |
| 2,119,325 | 5/1938 | Goodhart | 128/83 |
| 2,661,000 | 12/1953 | Gazeley et al. | 128/88 |
| 3,059,494 | 10/1962 | Grabowski | 74/424.8 R |
| 3,133,453 | 5/1964 | La Pointe | 74/424.8 R |
| 3,369,422 | 2/1968 | Sears | 74/424.8 R |
| 3,483,765 | 12/1969 | Fornataro | 74/89.15 |
| 3,769,636 | 11/1973 | Friedman | 128/25 R |
| 3,908,643 | 9/1975 | Bliss | 128/83 |

FOREIGN PATENT DOCUMENTS

| 2122284 | 11/1971 | Fed. Rep. of Germany | 74/424.8 R |
|---|---|---|---|
| 1487424 | 5/1967 | France | 74/424.8 R |
| 2365336 | 4/1978 | France | 128/80 |
| 329722 | 5/1930 | United Kingdom | 74/424.8 R |
| 1293452 | 10/1972 | United Kingdom | 74/424.8 R |
| 1356754 | 6/1974 | United Kingdom | 74/424.8 R |

*Primary Examiner*—Robert W. Michell
*Assistant Examiner*—Arthur S. Rose
*Attorney, Agent, or Firm*—Steele, Gould & Fried

[57] ABSTRACT

A guiding device for orthosis, comprising an anti-friction screw and nut assembly, in which the nut comprises two interconnected nut portions, which are rotatable but not axially displaceable relatively to each other, each nut portion having an axial bore for receiving said screw and at least two anti-friction bearings, each arranged to contact a thread groove of the anti-friction screw, said screw and one of said nut portions having means for attaching the same to an orthosis or to a support.

10 Claims, 6 Drawing Figures

ANTI-FRICTION SCREW AND NUT ASSEMBLY

The present invention relates to a screw and nut assembly serving as guiding or driving means for orthoses, especially arm orthoses, said assembly offering an extremely low friction between the screw and the nut. The invention further relates to an orthosis, especially a forearm orthosis, comprising such a screw and nut assembly.

In orthopedic appliances such as orthoses, i.e. permanent bandages or supports for damaged body parts, there is often a need for devices capable of guiding and/or driving the movement of a body part such that the patient repetedly can move the body part in a controlled manner. One problem is that the body part in question can be rather weak and unable to develope the necessary force. For example, patients suffering from intention tremor, especially in combination with ataxia, are often unable of doing general daily work such as eating, cooking, dishing, sewing, and so on.

The screw and nut assembly used in the present invention is virtually without friction between the screw and the nut. Futhermore, the nut is within broad limits independent of the pitch of the screw, and the nut can also be made independent of the thread direction of the screw.

When using such a screw and nut assembly as a guiding means for orthoses, in particular arm orthoses such as forearm orthoses, only very small forces will be required for obtaining the desired movements (because of the very low friction). It is also very simple to modify the nature of the movement with regard to the needs and desires in the specific situation, since the pitch of the screw can be varied without increasing the friction between the screw and the nut. Because of the low friction and the small forces required the orthosis can be provided with very compact and lightweight motors as driving means for causing the desired movement when the patient is unable to make the movement by his own muscle force. In such instances the motor can be driving either the nut or, preferably, the screw. The anti-friction nut according to the invention comprises two nut portions, which are connected in the axial direction, said portions being rotatable but not axially displaceable relatively to each other. Each nut portion has a central bore for a corresponding screw. The screw travels against at least two anti-friction bearings in each nut portion (but does not contact the walls of the central bore), each of said bearings engaging a thread groove of the screw. According to a preferred embodiment each nut portion is provided with two anti-friction bearings arranged opposite to each other. In this case the corresponding anti-friction screw preferably comprises two thread elements in the form of helical round bars of a suitable metal, which are attached to each other. The anti-friction screw has a great pitch angle, preferably at least 60°, especially at least 70°, and in particular at least 80°. The thread pitch can also be 90°, in which case the screw (or a portion thereof) turns to be a "bar" rather than a screw, said bar or bar portion then serving as a guide for a linear movement instead of a rotational movement. As mentioned above the same screw can have a locally varying pitch for obtaining the desired movement, and this may also include portions of 90° pitch angle. One or more of the thread elements may also be provided with a bend at a desired location, thereby making it possible to locally cause a heavy turn of the movement.

Figure 2:
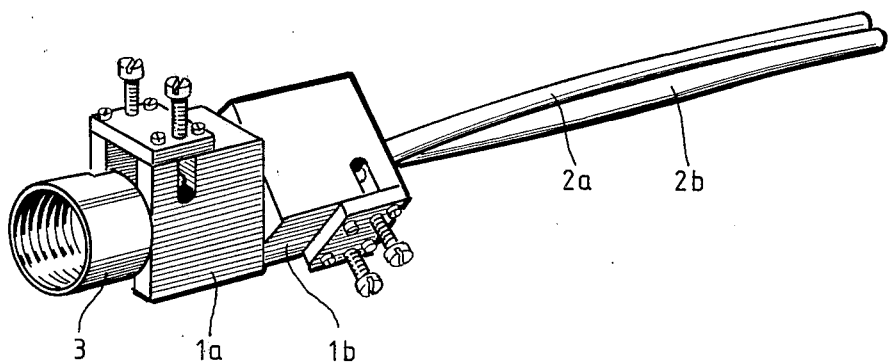
Figure 3:
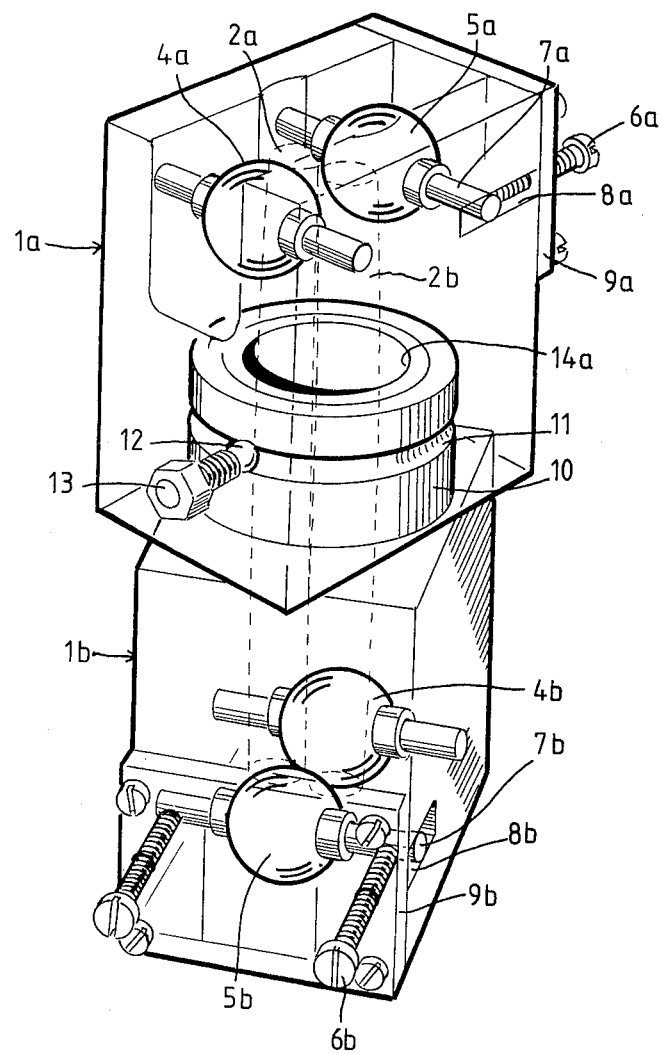
Figure 4:
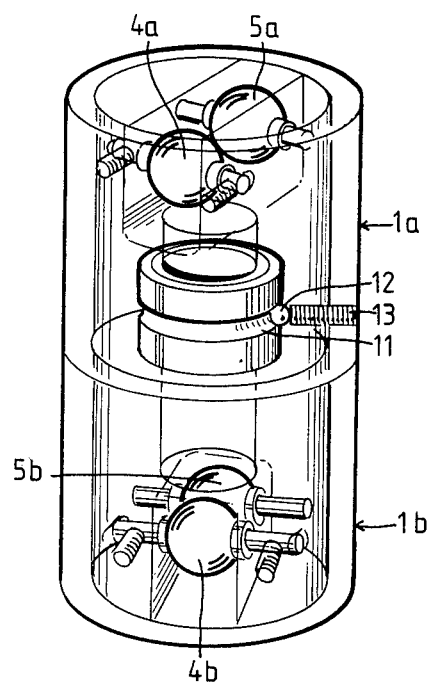
Figure 5:
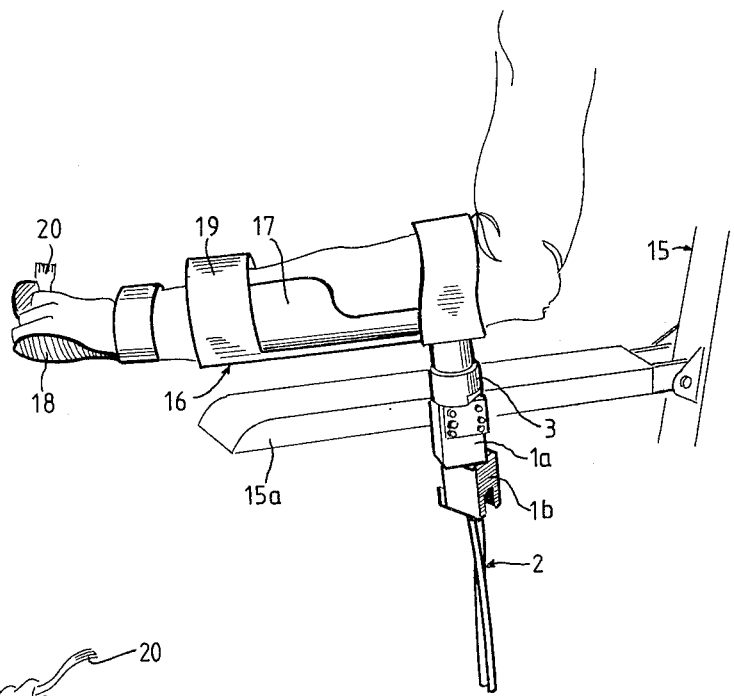
Figure 6:
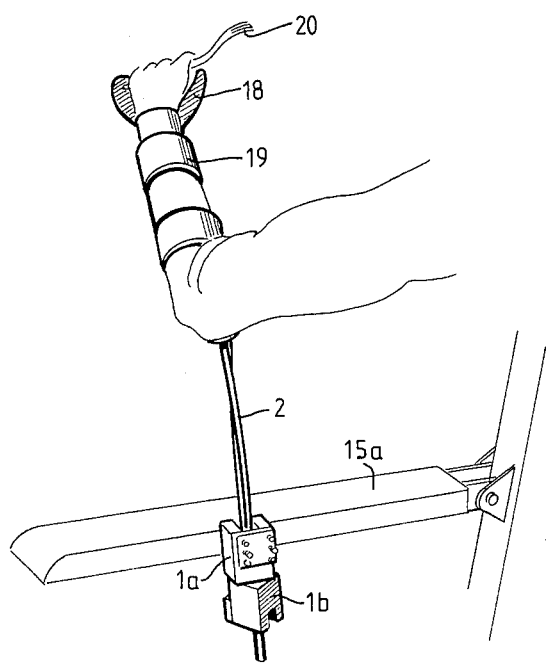

Some preferred embodiments of the invention—to which the same, however, is not limited—will be described below with reference to the enclosed drawings, in which FIG. 1 is a schematic perspective view of a first embodiment of an anti-friction screw and nut assembly according to the invention, FIG. 2 is a perspective view corresponding to FIG. 1 and showing the anti-friction nut in a different position along the screw, FIG. 3 is a schematic X-ray view showing the anti-friction nut according to FIGS. 1 and 2 in more detail, FIG. 4 is an X-ray view of a variant of the anti-friction nut according to FIG. 3, and FIGS. 5 and 6 are schematic perspective views showing two different positions of a forearm orthosis including a screw and nut assembly according to the invention as a guide means.

In FIGS. 1 and 2 there is shown an anti-friction nut 1 travelling on a corresponding screw 2 of very great pitch. The nut 1 comprises two nut portions 1a and 1b, which are rotatably connected to each other by means of any suitable anti-friction bearing. In the illustrated case the thread portion of the screw 2 consists of two helical thread elements 2a and 2b which are attached to each other in any suitable manner, e.g. by welding at regular intervals. The thread portions 2a, 2b preferably consist of two round metal bars of the same essentially uniform diameter. In the embodiment shown the screw 2 is at one end thereof provided with a connection head 3 for e.g. coupling the screw 2 to an orthosis to be guided and possibly driven by the screw, or alternatively to a support and/or a drive motor. One of the nut portions 1a and 1b is in a corresponding manner provided with suitable means for attachment to a support and/or drive motor, alternatively to the orthosis.

FIG. 3 shows the anti-friction nut of FIGS. 1 and 2 in more detail. As appears from FIG. 3 each nut portion 1a and 1b is designed as a housing for two anti-friction bearings 4a, 5a and 4b, 5b respectively. Said bearings are arranged in such a manner that both bearings in each pair of bearings—4a, 5a and 4b, 5b, respectively—will contact opposite threads between the thread elements 2a and 2b (which are shown schematically and in dashed lines in FIG. 3) of the screw 2 when the same is inserted in the respective nut portion 1a, 1b between said bearings. The bearings 4a, 5a, 4b, 5b can be of any anti-friction type such as spheric bearings, radial bearings, needle bearings, and so on. Radial ball bearings are the preferred type of bearing. In certain instances one of the bearings (or possibly both bearings) in either or both of the pairs of bearings 4a, 5a and 4b, 5b respectively can be spring biased against the screw threads, whereby it is possible to compensate for irregularities or non-uniformness of the same.

In the embodiment shown the bearings 4a and 4b are in fixed positions in the respective housing, whereas the distance from the bearings 5a and 5b to the opposite bearings 4a and 4b respectively can be adjusted by means of set screws 6a and 6b respectively. To this end the shafts 7a, 7b of the bearings 5a, 5b are journalled in slots 8a, 8b in the respective housing, and they can be displaced in the slots 8a, 8b by adjustment of the set screws 6a, 6b. The latter engage corresponding threads provided in cover plates 9a, 9b, which are secured to the respective housing after the bearing shafts 7a, 7b have been inserted in the slots 8a, 8b.

The lower nut portion 1b of FIG. 3 is provided with a central, upwardly projecting bearing sleeve 10 projecting into a corresponding, centrally arranged recess in the lower part of the upper nut portion 1a. The sleeve 10 is at its outer side provided with a peripheric groove 11, the shape of which is adapted to at least one bearing ball 12. The (or each) ball 12 is located between the groove 11 and a set screw 13 carried by the nut portion 1a and located opposite to the groove 11. When the sleeve 10 of the nut portion 1b is inserted into the corresponding recess in the nut portion 1a, then the bearing ball 12 will engage the groove 11 as well as a corresponding bearing site provided at the inner end of the set screw 13. In this manner the ball (or balls) 12 will prevent translational movements of the nut portion 1a with respect to the nut portion 1b, while at the same time permitting rotation of said portions with respect to each other. The clearance of the ball 12 is adjusted by means of the set screw 13 so as to obtain as little friction as possible upon rotation while still prohibiting translational movements.

The screw 2 is intended to travel through the nut portions 1a, 1b with the pairs of bearings 4a, 5a and 4b, 5b contacting the thread grooves formed between the thread elements 2a, 2b. The nut portions 1a and 1b are coaxial and have central bores 14a, 14b, which are preferably big enough to allow the screw 2 to freely pass through the nut portions 1a, 1b and contact the same only at the bearings 4a, 5a and 4b, 5b respectively.

The anti-friction nut shown in FIG. 4 corresponds to the one shown in FIGS. 1 to 3 with the exception that the housings for the bearings 4a, 5a, 4b, 5b are of tubular shape.

FIGS. 5 and 6 illustrate the use of the screw and nut assembly of FIGS. 1 to 3 as a guide means for a forearm orthosis. One of the nut portions (in this case 1a) is attached to the arm rest 15a of a chair 15 (which may be a wheel chair). The connection head 3 of the screw 2 is attached to a forearm orthosis 16 in the vicinity of the elbow portion thereof. The orthosis 16 comprises a forearm support 17, a hand support 18 and attachment ships 19—e.g. interlocking fibre strips such as Welcro ®type strips—for keeping the forearm of the patient in place in the forearm support 17.

FIGS. 5 and 6 illustrate, as an example only, the use of the orthosis 16 for eating.

In the starting of FIG. 5 the orthosis 16 is located such that the patient with a fork 20 can take food from a plate. In this position the connection head 3 of the screw 2 preferably rests on the nut portion 1a. For moving the fork 20 to the mouth, i.e. to the position illustrated in FIG. 6, there is only required an extremely small force because of the practically non-existing friction between the screw 2 and the nut 3, thereby making it possible even for weak patients to make the desired movement. The movement from the position according to FIG. 5 to the position according to FIG. 6 is decided by the design of the screw and nut assembly 2, 3, the nature of the movement mainly being determined by the pitch of the screw 2. By varying the pitch (and/or the position of attachment of the screw 2 to the orthosis 16) it is in a very simple manner possible to "tailor make" the guide means for each individual patient. In the orthosis shown the pitch is about 88°.

The invention is, of course, not restricted to the embodiments described above and especially shown in the drawings, but many modifications and variations are possible within the scope of the general inventive idea. For example, the connection head 3 (or any other suitable attachment means) may be connected to any suitable, preferably rotationally reversing driving source for obtaining an extremely power saving repeated drive of the orthosis 16 between the positions shown in FIGS. 5 and 6. The orthosis may in certain instances also be attached to the nut, the screw then being attached to the support. Although the anti-friction nut preferably is combined with an anti-friction screw of the indicated type, i.e. a screw consisting of two helical round metal bars secured to each other, it is, of course, also possible to use other types of screws, such as corresponding screws having e.g. three or four such thread elements. As mentioned above it is also possible to use "screws" having a pitch angle of 90° serving as rails or bars and which may be provided with desired bends or curves. Thanks to the rotatability between the two nut portions the anti-friction nut according to the invention does not either require a constant thread pitch of the screw, and as a result it is possible to vary e.g. the thread pitch locally, as may be desired. In this manner there will be great possibilities for adjusting the guiding movement, provided by the screw and nut, to the needs and desires in the individual situation.

What we claim is:

1. An orthosis arranged to be attached to an external support, said orthosis comprising: a rigid support for a body part; means for keeping the body part in place in said support; guiding device attached to said support, wherein said guiding device comprises an anti-friction screw and nut assembly, in which the nut comprises two interconnected nut portions being rotatable but not axially displaceable relative to each other, each nut portion having an axial bore for receiving said screw, and at least two anti-friction bearings arranged symmetrically with respect to said bore, each bearing being arranged to contact one thread groove of said screw.

2. An orthosis according to claim 1, wherein said screw is attached to said body part support, and wherein one of said nut portions is arranged to be attached to said external support.

3. A device according to claim 2, wherein said anti-friction bearings are spherical bearings.

4. A device according to claim 3, wherein said anti-friction bearings in each nut portion are arranged pairwise and essentially opposite to each other.

5. A device according to claim 4, further comprising means for adjusting the distance between opposite anti-friction bearings.

6. A device according to claims 1 or 2, wherein said anti-friction screw comprises at least 2 thread elements designed as helical round bars of essentially the same diameter, which are attached to each other such that thread grooves fitted to said anti-friction bearings are formed between adjacent thread elements.

7. A device according to claim 6, wherein the pitch angle of the anti-friction screw is at least 60°.

8. A device according to claim 6, wherein the pitch angle of the anti-friction screw is at least 70°.

9. A device according to claim 6, wherein the pitch angle of the anti-friction screw is at least 80°.

10. An orthosis according to claims 1 or 2, wherein said rigid support is a forearm support attached to one end of said screw, and one of said nut portions is arranged to be attached to a fixed support such as the arm rest of a chair.

* * * * *